United States Patent
Grodzins et al.

[11] Patent Number: 5,696,806
[45] Date of Patent: Dec. 9, 1997

[54] TOMOGRAPHIC METHOD OF X-RAY IMAGING

[76] Inventors: Lee Grodzins, 14 Stratham Rd., Lexington, Mass. 02173; Charles G. Parson, P.O. Box 430, Nutting Lake, Mass. 01865

[21] Appl. No.: 613,492

[22] Filed: Mar. 11, 1996

[51] Int. Cl.$^6$ ................................................. G01N 23/201
[52] U.S. Cl. ........................... 378/86; 378/87; 378/88
[58] Field of Search ........................... 378/86, 87, 88, 378/89, 90, 51, 53, 54, 57

[56] References Cited

U.S. PATENT DOCUMENTS

| | | | |
|---|---|---|---|
| 5,179,581 | 1/1993 | Annis | 378/86 |
| 5,420,905 | 5/1995 | Bertozzi | 378/86 |
| 5,430,787 | 7/1995 | Norton | 378/87 |

*Primary Examiner*—Don Wong

[57] ABSTRACT

A method is disclosed for obtaining the density distributions of three-dimensional elements that compose objects or groups of objects, by examining the objects with beams of x-rays or gamma radiation that are transmitted through the object in a plurality of approximately parallel paths and measuring the intensity of the radiation, scattered approximately perpendicular to the parallel paths, in arrays of detectors around the object. The energy of the x-rays or gamma rays is such that dominant interaction in the object is Compton scattering. The density of each element is determined from the totality of measurements by standard mathematical tomographic or relaxation techniques of data manipulation.

17 Claims, 4 Drawing Sheets

TOMOGRAPHIC METHOD OF X-RAY IMAGING

BACKGROUND OF THE INVENTION

1. Field of the Invention

This invention relates to the examination of a body by means of x-radiation or gamma radiation.

2. Description of the Prior Art

The creation of images of x-ray attention coefficients through objects began with the discovery of x-rays by Roentgen in 1895 and has developed continuously. A major advance was the invention in the early 1970's, by GN Hounsfielch of computerized axial tomography, CAT. (U.S. Pat. Nos. 3,778,614, 4,035,647). Hounsfield showed that the linear attenuation coefficients of individual elements in an object could be reconstructed from the measurements of the intensities of x-ray beams that pass in a plurality of independent paths through the object. Since Hounsfield's invention, the technology of CAT scanning has developed in a number of ways, but all x-ray methods deduce the density distributions from measurements of the radiation transmitted through the object.

SUMMARY OF THE INVENTION

This invention is a method for determining the densities of objects or the distribution of densities interior to an object by measuring the intensities of x-rays that are Compton scattered from the volume elements (voxels) of the object. The term x-rays is used throughout the descriptions since it is anticipated that most applications will use an x-ray beam generated by energetic electrons inn an x-ray tube, but it should be evident that all types of energetic photons can be used, including monoenergetic gamma rays, that satisfy the criterion that the energy of the photons are such that Compton scattering dominates the interactions of the photons in the object. The use of scattered radiation to determine densities is fundamentally different in theoretical underpinning, in methodology and in implementing apparatus from the standard methods that use transmitted x-rays to determine densities of interior voxels.

The incident x-rays are rastered across at least one face of an object. The x-rays that are Compton scattered approximately perpendicular to the beam directions are detected in arrays of collimated detectors each of which is sensitive to radiation scattered from a specific portion of the incident x-ray beam.

The distinctive features of the preferred embodiment of this invention are: 1) The energy of the x-rays is high enough so that the interactions in the object are dominated by the Compton effect. In particular, the energy is high enough so that the photoelectric interaction makes a minor contribution in the analysis but it is not so high that pair production is significant. 2) The incident x-rays are collimated into a beam that is scanned through the object in a series of contiguous, approximately parallel paths; the scanning may be accomplished by moving the beam or the container or a combination of both so that the incident x-ray beam passes through every voxel that the detected scattered radiation passes through. 3) The scattered x-rays are detected by arrays of counters that distinguish x-rays that are scattered approximately perpendicular to the incident radiation. The detectors must be capable of sensing the direction of the scattered radiation. Methods for sensing the direction of an incident x-ray are well known; gamma cameras, for example, do so with collimators and position-sensitive detectors. 4) The volume element resolved by this invention is determined by the cross sectional area of the incident x-ray beam times the spatial resolution along the beam path of the origins of the scattered x-rays. The total number of independent measurements is at least equal to the total volume being examined divided by the volume element of spatial resolution. 5. The densities of the voxels is rapidly and accurately determined from the totality of measurements by standard mathematical relaxation methods, without the need for transformation into frequency space or the use of back projection, though both of those techniques can be used.

This invention, which we will refer to as Compton Scatter Tomography or CST, is a new modality for tomography, quite distinct from the conventional method of computerized axial tomography, CAT, in which the linear attenuation coefficients in voxel elements in an object are determined from transmission measurements, or Single Photon Emission Computer Tomography, SPECT, in which the directions of gamma rays emitted from a radioactive source distributed in a body is used to measure the distribution of radioactivity. The invention is described in its application for the inspection of containers for contraband such as explosives. It should be appreciated, however, that this invention may be useful for a broad range applications in which a non-destructive method is needed to determine the density distributions of objects.

EMBODIMENT EMPLOYING MONOENERGETIC GAMMA RAYS

The invention is first described using a monoenergic gamma ray source, in particular the 662 keV gamma ray from the decay of $^{137}$Cs. Other radioactive sources, such as the 356 keV gamma ray from the decay of $^{133}$Ba, or the 1117 keV and 1332 keV gamma rays from $^{60}$Co, or monochromatic x-ray sources might be appropriate for specific applications but $^{137}$Cs is an especially appropriate choice because of its long 30 year half-life, low cost, high specific activity and simplicity of its radiation spectrum.

Figure 1:
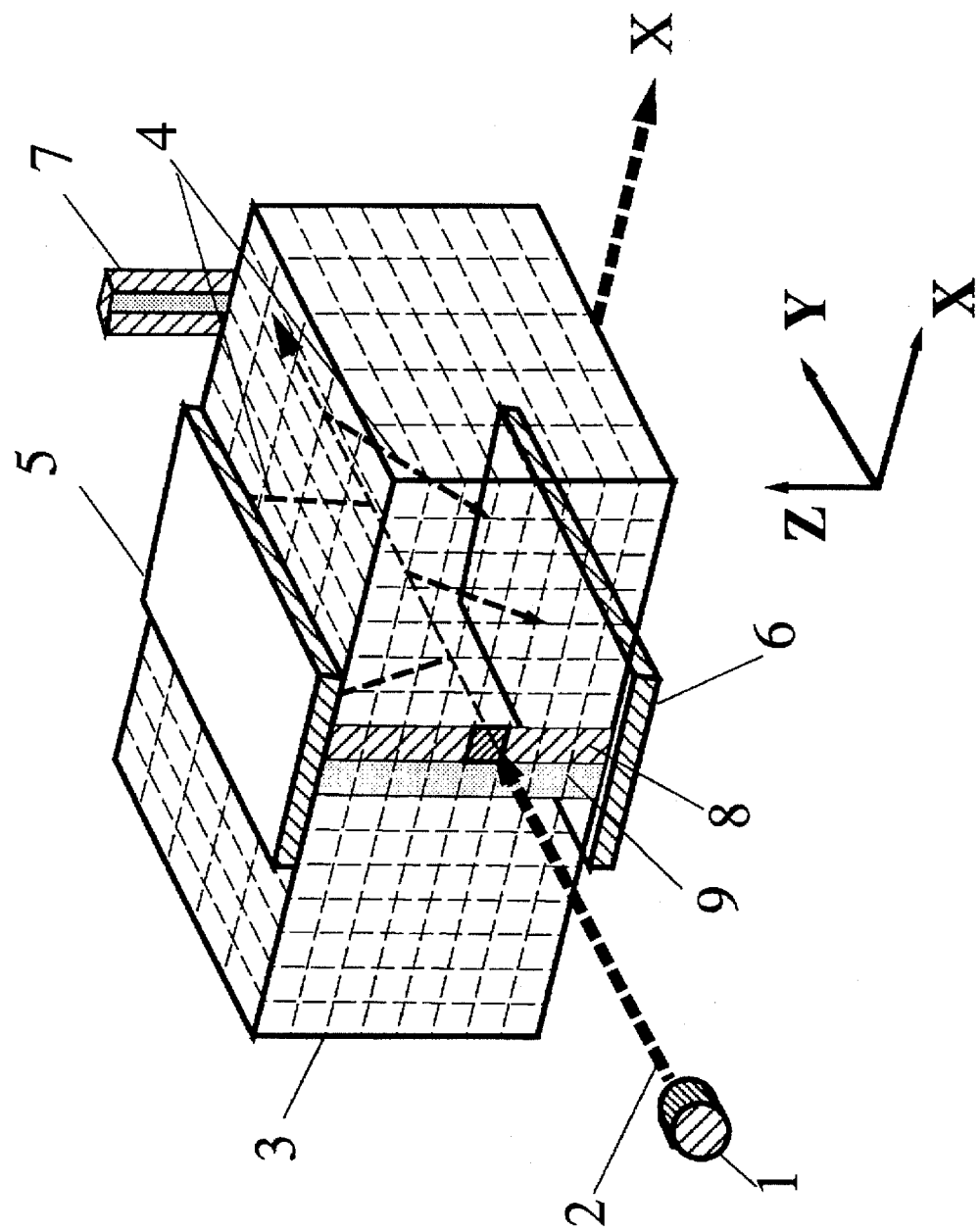
FIG. 1. A schematic drawing of the main elements of a preferred embodiment of the invention. A beam of x or γ-rays 2 directed along the Y axis is stepped in a series of approximately parallel paths in the YZ plane so as to intersect every voxel in the plane 8 of the container 3. The examined container moves in the X direction. The x-rays 4 scattered through approximately 90° by elements in the container are counted by an array of collimated detectors 5 and 6, above and below, respectively, the container. A detector 7 of the transmitted x-rays is also shown.

FIG. 1 shows the essential features of the invention as it might be applied to determining the density distributions of materials in luggage. The 662 keV gamma rays from the radioactive source 1 of $^{137}$Cs, are collimated into a beam 2, which is aimed in the Y direction into the luggage 3. The luggage 3 is conveyed in the X direction, i.e., perpendicular to the direction of the beam 2. The intensity of gamma rays 4 that are Compton scattered through approximately 90° in the ±Z directions are measured in top and bottom detectors 5 and 6. The collimated beam 2 is incrementally moved in the Z direction to an adjacent row of voxels in the slice 8 and the measurements repeated until the x-ray beam has interacted with every voxel in the full YZ slice 8 of the luggage 3. The luggage is then moved incrementally in the X direction and the adjacent slice 9 is investigated. In this way, the entire container is examined. It will be appreciated that any combination of relative motions of the gamma ray beam with respect to the luggage is acceptable, including stationary luggage with all of the relative motion supplied by a raster scanned beam and the converse, a stationary beam with all of the relative motion supplied by a luggage conveyance. It will also be appreciated that the relative motions may be incremental or continuous depending on the application. The central requirement is that every voxel in the volume being interrogated must be traversed at least once by both the incident and scattered radiation. The detectors of scattered radiation 5 and 6 may each be single large volume detectors that have the energy and angle dispersive power to determine both the energy of the Compton scattered radiation and the direction from which it came. Such detectors are being developed with these capabilities, but at this time a more cost-effective solution is to use segment detectors 5 and 6 into arrays of collimated detectors each of which is sensitive to radiation from a particular voxel along the beam 2.

Figure 2:
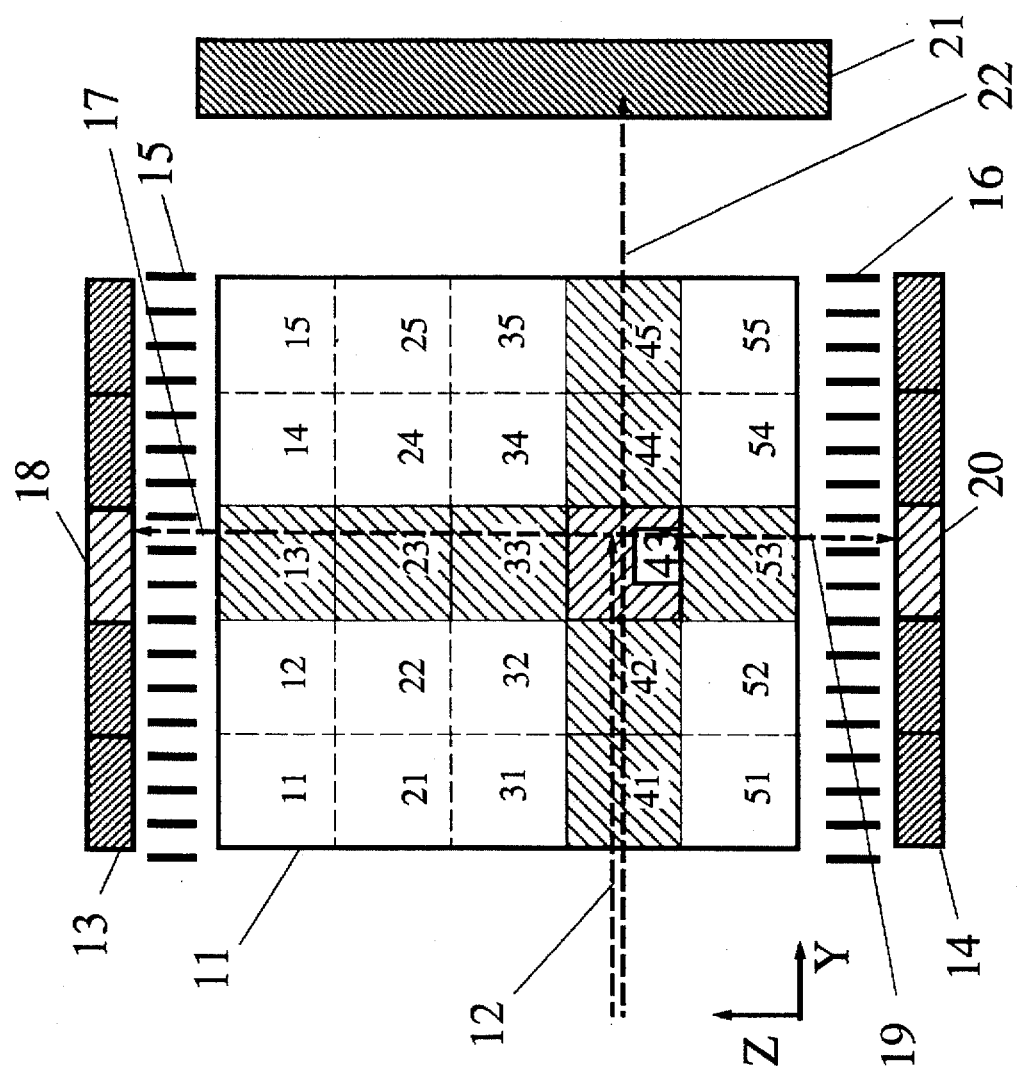
FIG. 2. A cross section of the container showing one plane of the container, such as plane 8. The area of the plane is divided into 25 imaginary voxels. The incident x-ray beam 12 passes along the fourth row and is shown scattered in voxel 43 into the upper detector 18 and the lower detector 20. The transmitted beam is shown stalking the detector 12.

FIG. 2 shows one slice 8 of the luggage imagined to be divided into 5 rows and 5 columns to make a total of 25 voxels. The voxels are numbered sequentially, 11, 12, 13, 14, 15, 21, 22, etc. The 662 keV beam of gamma rays 11 is shown passing along the fourth row, through voxels, 41, 42, 43, 44 and 45 to the transmission detector 21. The gamma rays that are scattered in the voxels of row 4 are counted in the top detector array 13 and the bottom detector array 14 which have appropriate collimators 15 and 16 to ensure that only scatterings through ~90° are detected. The voxels are assumed to be cubic; in practice, the size of the voxels will depend on the beam cross section, beam divergence and the spatial resolution of the detector arrays. FIG. 2 shows an example of Compton scattered radiation 17 being scattered in the Z direction from pixel 43 into the single detector 18 and another scattering 19 in the -Z direction into detector 20.

The scattering of the 662 keV gamma ray through 90° results in 288 keV radiation. The intensity of the 288 keV signal, $I_{17}$, in detector 18 is given by:

$$I_{17(288)} = I_o(662) e^{-(\lambda_{41}t_{41}+\lambda_{42}t_{42})662} \left[ \frac{d\lambda_{43}^{Comp}(662)}{d\Omega} d\Omega\left(\frac{\pi}{2}\right) t_{43} \right] e^{-(\lambda_{33}t_{33}+\lambda_{23}t_{23}+\lambda_{13}t_{13})288} \quad 1)$$

where $I_o(662)$ is the intensity of the incident beam 11, the $\lambda$ values in the first exponential are the total linear attenuation coefficients for 662 keV radiation, the $\lambda$, values in the second exponential term are the total linear attenuation coefficients for the scattered radiation of ~288 keV, the t values are the linear dimensions of the pixels, and the square bracket term is the probability for Compton scattering in pixel 43. The linear attenuation coefficients are defined in terms of the cross section σ, the atomic weight A, Avogadro's number $N_o$, and the density ρ;

$$\lambda = \sigma \frac{N_o \rho}{A} \quad 2)$$

An analogous equation to 1 can be written for the intensity scattered into detector 20; only the last exponential term and the solid angle factor changes. There will be a total of 10 equations describing the scattering from material along row 4 into the segmented detectors in the top 13 and bottom 14 arrays. Each row that the 662 beam traverses will produce 10 more independent equations. A total of 50 equations will be generated in a full scan of the slice 8. An additional 5 equations will be generated by the intensities in the transmission detector 12; the equation for the ray 12–22 shown in FIG. 2 is given by, $$I_{22}(662) = I_o(662) e^{-(\lambda_{43}t_{41}+\lambda_{42}t_{42}+\lambda_{43}t_{43}+\lambda_{44}t_{44})} \quad 3)$$

The transmission intensities exampled by Equations 3 are not necessary for solving Equations 1 for the densities in each of the volumes of the container 12, but they give important additional information that can speed up and make more secure the analytic procedures.

Figure 4:
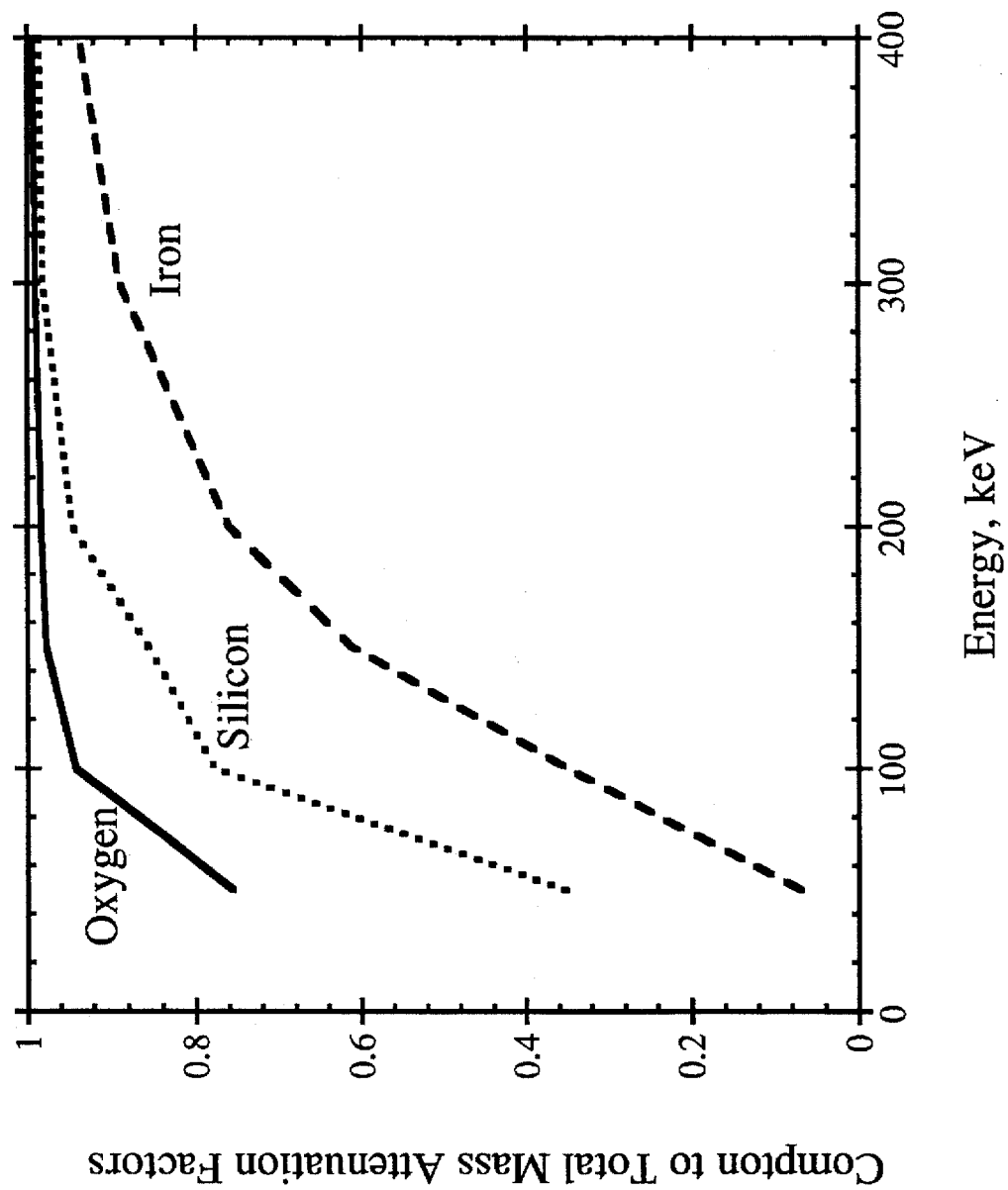
FIG. 4. A plot of the ratio of the Compton mass attenuation factor to the total mass attenuation factor as a function of x-ray energy, for oxygen, silicon and iron.

In the preferred embodiment using $^{137}$Cs, the interactions in the container are dominated by the Compton effect. FIG. 4 shows that the Compton effect in iron, the heaviest of the materials found in luggage in substantial quantities, accounts for 98% of the interactions for the incoming radiation of 662 keV and 88% of the interactions for the 288 keV scattered radiation. Equations 1, 2 and 3 then simplify enormously since, $$\lambda = \lambda_{Compton} + \lambda_{photoeffect} + \lambda_{Rayleigh} + \lambda_{pair\ production} \cong \lambda_{Compton} \quad 4$$

and the differential Compton attenuation $$\frac{d\lambda_{43}^{Comp}(662)}{d\Omega}$$

for 90° scattering of 662 keV gamma rays is simply related to the total linear attenuation, $$\frac{d\lambda_{43}^{Comp}(662)}{d\Omega} = 0.04\ \lambda^{Comp(662)}. \quad 5)$$

The consequence of these simplifications, all of which follow from the use of sufficiently high energy photons, is a set of 50 scattering equations and 5 transmission equations that contain just 25 unknowns, the 25 Compton linear attenuation coefficients. Equation 1, for example, becomes, $$I_{17}(288) = I_o(662)e^{-(\lambda_{41}{}^c + \lambda_{42}{}^c)662} \left[ .04\, \lambda^c(662) d\Omega \left( \frac{\pi}{2} \right) t_{43} \right] e^{-(\lambda_{33}{}^c r_{33} + \lambda_{23}{}^c r_{23} + \lambda_{13}{}^c r_{13})} \qquad 6)$$

where all of the unknown quantities in the inspection of a container are total linear Compton attenuation coefficients which depend primarily on the densities in the voxels.

The 50 scattering equations in this example can be rapidly solved by relaxation techniques; it is not necessary to use matrix inversions or convert to frequency space. To emphasize the simplicity we note that the equations describing the interaction of the beam with the top row of voxels of FIG. 2 (voxels 11 through 15) result immediately in the densities of each of the voxels since the scattering from voxel 11 is described by an equation with only 1 unknown, the density of the voxel. The scattering from voxel 12 is described by an equation with only 2 unknowns, one of which has been determined from the scattering from voxel 11, and so forth. Thus a series of simple iterations results in the linear Compton attenuation values for all of the voxels. In practice, one would use the values of the 50 intensifies of scattered radiation and 5 intensities of transmitted radiation to determine a first-order map of the $\lambda$ values in the 50 voxels and then use mathematical relaxation techniques to obtain a best set of density values. It should be noted that the method results in at least twice as many independent equations as the minimum required for a full tomographic analysis. These extra equations, plus the transmission equations 3, can be used to make the corrections to the scattering equations, such as Equation 6, to take into account small contributions of photo-electric absorption or coherent scattering that are present when the voxels contain higher Z material.

The linear Compton attenuation coefficients are directly proportional to the electron densities in the voxels; i.e., Equation 2 simplifies to Equation 8.

$$\lambda^c = \sigma^c Z \frac{N_o \rho}{A} = \sigma^c \times \text{number of electrons per volume} \qquad 8)$$

where $\sigma^c$, the Compton scattering per electron, is a constant, and Z is the number of electrons per atom. The electron densities are, in turn, very closely related to the matter densities since, for most materials in luggage, $Z/A \cong 0.5$. (The avenge value of $Z/A$ for plastics, explosives and other light materials is a few percent greater than 0.5; $Z/A$ for heavier materials such as iron are a few percent less.)

EMBODIMENT EMPLOYING POLYENERGETIC X-RAYS

Figure 3:
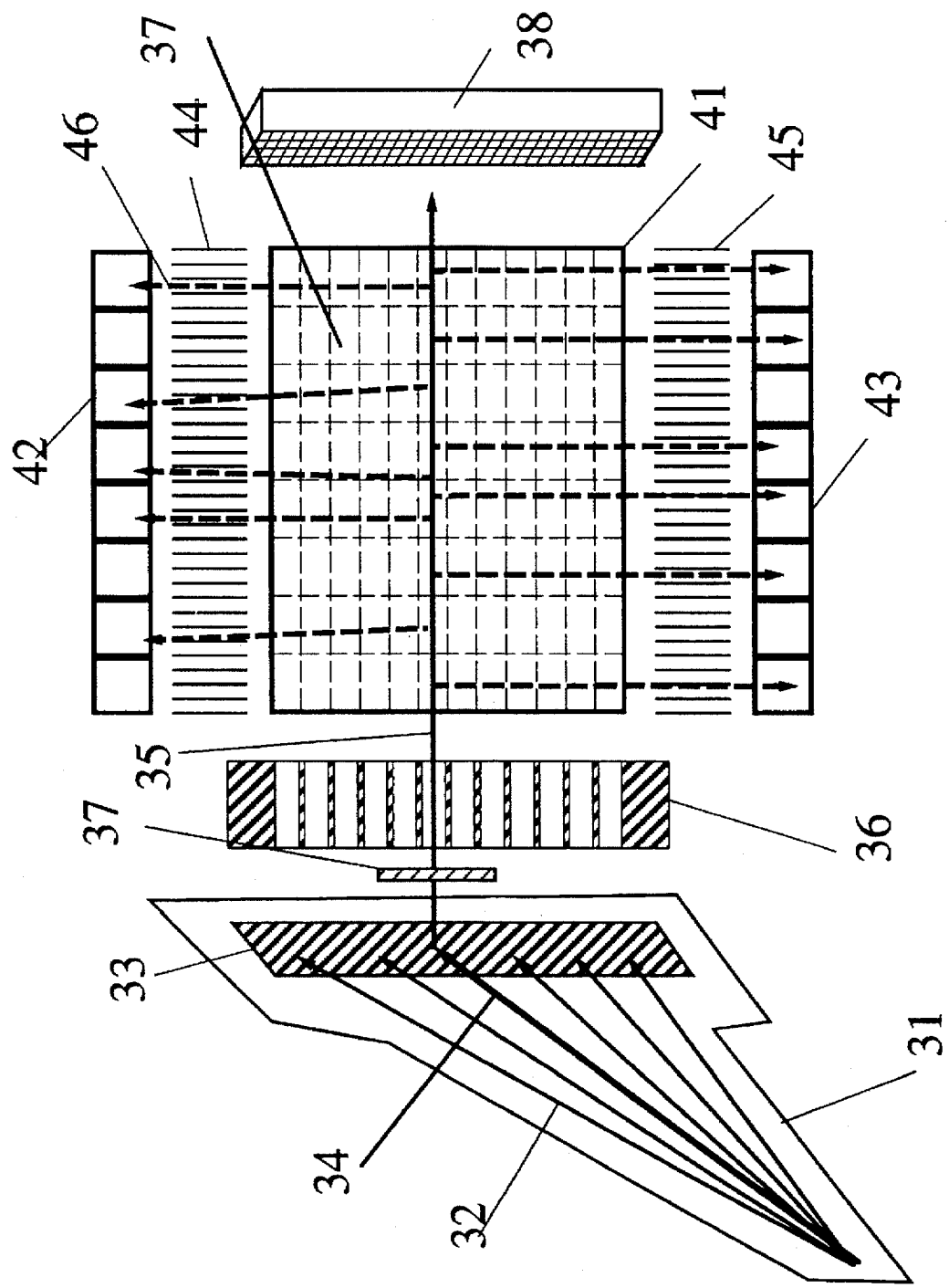
FIG. 3. A cross section view of the main elements of the invention showing an x-ray machine 31 that generates a raster scanned beam of electrons that strike the anode 33. The electron beam 32 is shown striking the top of the anode 33; the electron beam 34 is shown striking near the midpoint of the anode 33. The electron beam 34 generates x-rays that are collimated into a beam 35 by the collimator 36. The x-ray beam 34 passes through the container 41. Some of the x-ray beam is scattered through approximately 90° into arrays of collimated detectors 42 and 43 that are above and below the container, respectively. The x-ray beam that transmits the container 41 is detected in a segmented detector 38.

It is anticipated that the invention will usually be implemented using a spectrum of x-rays generated by an electron beam. The source of the x-rays could be a conventional x-ray tube with a fixed electron beam striking a fixed or rotating anode. Our preferred embodiment uses a raster scanned electron beam shown schematically in FIG. 3. The x-rays are generated in a x-ray tube 31, which produces a raster-scanned beam of x-rays by scanning the electron beam 32 and placing an appropriate collimator 36 in front of the anode 33. The x-ray tube 31 is similar to a conventional cathode ray tube with an appropriate heavy element anode 33 replacing the traditional phosphor screen. As the electron beam sweeps across the anode 33, x-rays are generated that pass through successive parallel holes in the collimator 36. The result is a rastering of approximately parallel beams of x-rays through the container 41. The anode potential determines the maximum energy of the x-ray beams. An absorber 37 eliminates the softer components of the x-ray beam and determines the effective lower energy of the x-rays that interact in the container.

It should be emphasized that the choice of anode voltage and x-ray strength depends on the application. Large containers might warrant anode voltages as high as 2 MeV (pair production is still negligible at this energy) in order to produce sufficiently penetrating x-rays, while small containers with primarily low Z components might be studied effectively with x-ray energies below 150 keV.

A practical choice of parameters for scanning airport luggage would be an anode potential of 450 keV and an electron current of 4 milliamps. The length of the anode 33 might be 20", i.e., about the height of the anode of a 30" TV tube; a power density of 2 kilowatts is easily handled by modest cooling of the large-area. The collimator 36 might be a set of parallel holes in a 4" thick lead block (attenuation by the lead$>10^{10}$). The holes should be appropriately designed to minimize internal scattering in the collimator. The absorber 37 might be 1 mm of tungsten that would reduce the 300 keV x-rays by a factor of ~2 while killing 100 keV components by factors of $10^4$.

Above and below the container are detectors or detector arrays 42 and 43, respectively that measures the scattered x-rays 46 as a function of position of scattering along the beam direction. To do this, we propose to use collimating slits 44 and 45 such as the Soller plates used extensively in x-ray diffraction. These slits restrict the direction of x-rays seen by the detector; their function is similar to the collimators used in Single Photon Emission Tomography (SPECT) in which the origins of the emission of gamma rays from radioactive sources is determined by the SPECT detector. Many options are available for the detectors including the hodoscopes of NaI(Tl), BGO and CdZnTe now used for SPECT and Positron Emission Tomography.

Equations 1 and 3 must now be written in terms of weighted integrals over the energy spectra. Exact expressions can be taken into account in the analysis, though we anticipate that in most practical cases it will be sufficient to use appropriate averages of the incident and scattered energies as well as the differential and integral linear attenuation coefficients in Equations 1 and 3, since the Compton cross sections vary slowly with energy, atomic number, and scattering angle around 90°. Specifically, for elements from carbon to iron, the total Compton cross section varies by only 25% from 150 keV to 450 keV; for a given x-ray energy, it varies by only 10%. Moreover, the differential Compton cross section is almost independent of angle from 80° to 110°. It should also be noted that beam hardening—the changing energy spectrum in the container due to absorption—will not be significant when the invention is applied to airline baggage since the high energies of the incident beam are not much attenuated traversing an airline suitcase.

We have carded out computer simulation studies, assuming a rastered x-ray beam with dimensions 5 mm×5 mm generated by a 2 kilowatt, 450 keV electron beam. We estimate that efficient side scattered detectors can determine the origin of the scattered x-rays to within 2 cm along the beam path. (Note that SPECT hodoscopes of 150 keV radiation have spatial resolutions of approximately 0.5 cm.) Each voxel thus has a volume of 0.5 cc so that 100 grams of explosives would occupy about 300 voxels. The simulation studies show that the interrogation of a piece of luggage, 1 meter×60 cm×20 cm can be carried out in 6 seconds, resulting in the determination of the linear attention coefficients of each voxel in the luggage to an accuracy of 30%. The mean values of the densities of any contiguous 300 voxels (~100 g of explosives) would then be known to an accuracy of 2%. The simulation studies show that CST should have a minimum detection limit below 100 g of explosives.

It should also be noted that the CST method of tomographic analysis is very effective for finding sheet bombs, one of the most difficult of the explosive configurations to investigate by x-ray means.

A logical extension of the invention is to make scattering measurements at two incident energies, one at the preferred high energy where the Compton effect is dominant and the other at a lower energy where the photo-electric effect makes a substantial contribution to the interactions of the x-rays in those voxels with high Z components. This so-called dual-energy method is well know for transmission tomography where it is used to determine the effective atomic number of the elements in the voxels and we anticipate that the dual energy method could have applications in which the measurement of the effective atomic number of the voxels as well as the density is important. Referring to FIG. 4, one might choose a high x-ray energy greater than 300 keV where the Compton effect is more than 90% of the total interaction in iron, and a low energy x-ray in the 100 keV range where the photo-electric effect makes up about 80% of the cross section in iron. Dual energy, however, is not so easily applied to CST where the scattered radiation is substantially lower than the incident energy; e.g., the energy of Compton scattered 300 keV x-ray is 188 keV, and the energy of the Compton scattered 100 keV x-ray is 83 keV. The change in the energy in the former case makes only a minor, and easily accounted for, complication to the analysis. The change in the latter case is not so easily taken into account since small changes in the scattered energy make large changes in the attenuation coefficients. The effects of beam hardening—that is, the increase in the average energy of the beam as the lower energy components become absorbed in the container—are very difficult to take into account. Nevertheless, there may be applications for this extension, particularly when only a relatively few voxels contain high Z material.

The invention stresses that the incident beams should be rastered across the container in approximately parallel paths and that the detected radiation should be limited to those x-rays that are scattered approximately perpendicular to the incident beam direction. The allowable deviations from these conditions depend on the applications. For all applications we expect that the deviations can be at least ±20°, since the cos 20° deviates by only 6% from unity. For some applications, especially those in which the high density regions make up a small portion of the container, the deviations from ideal could be considerably larger. Simulation studies indicate that the CST method is robust with respect to deviations from parallel beams and 90° scattering but that the closer the rastered beams are to being parallel, and the closer the scatter angle of detected rays are to 90°, the simpler and more accurate will be the analytic tomographic procedures for determining the densities.

We claim:

1. A method for determining a three-dimensional density, distribution among volume elements in a volume containing at least one material, the method comprising:

a. producing a beam of energetic photons for penetrating the volume;

b. scanning the beam sequentially across incremental positions of the volume in a plurality, of paths having substantially parallel directions separated by incremental steps;

c. detecting scattered photons of substantially all energies scattered by the material in said volume with a detector having a spatial resolution in a direction substantially parallel to the paths of the beam;

d. measuring the intensity of scattered photons scattered approximately perpendicular to each substantially parallel direction of the beam at each incremental position of the beam to derive an independent measurement of intensity, of scattered photons scattered from the volume elements in the volume;

e. identifying a volume element as the approximate origin of scattering along the path of the beam giving rise to the measurement of intensity of scattered photons; and f. calculating an independent density for each volume element of the material in the volume.

2. A method according to claim 1, in which the size of each volume element in the volume is determined by the diameter of the beam that traverses said volume element, the step size of the incremental steps of said beam, and the spatial resolution of the detector substantially parallel to the beam path.

3. A method according to claim 1, in which the number of independent measurements of the intensity of scattered photons scattered from the volume elements in said volume is at least approximately equal to the number of volume elements.

4. A method according to claim 1, in which the intensity, of each beam transmitted through the volume is measured together with the intensity of said scattered photons scattered by the material.

5. A method according to claim 1, in which the energies of the energetic photons in each beam are in an energy range where the interaction of the energetic photons with the material is dominated by the probability for Compton scattering.

6. A method according to claim 1, in which the step of calculating the density of each volume element of the material in the volume includes a mathematical relaxation procedure in which a first trial function in the mathematical relaxation procedure uses the independent measurements of the intensity, of scattered photons scattered from the volume elements in the volume.

7. A method according to claim 1, in which the density distribution among the volume elements in the volume is determined by a computerized tomographic reconstruction procedure having a number of independent measurements at least equal to the number of independent densities calculated in the step of calculating.

8. A method according to claim 1, in which the step of scanning the beam sequentially across incremental position of the volume includes scanning a first beam and a second beam, the first beam having a first mean energy high enough so that the Compton interaction dominates the interaction of the first beam with the material, and the second beam having a mean energy low enough so that the photoelectric interaction makes a significant contribution to the interaction of the second beam with at least some material in the volume, such that the intensity of scattered radiation from the first and second beams are used to determine the effective atomic number of the at least one material in the volume by a mathematical reconstruction technique.

9. A method according to claim 8, wherein the mathematical reconstruction technique includes relaxation methods.

10. A method according to claim 8, wherein the mathematical reconstruction technique includes methods of computerized tomographic reconstruction.

11. A device for determining densities in volume elements in a material present in an assembly of objects, the device comprising:
   a. a source for producing a beam of energetic photons having a direction for penetrating the material;
   b. an arrangement for scanning the beam of energetic photons in a sequence of sequential beams across the assembly in a manner such that successive directions of the sequential beams are substantially parallel to each other, the sequential beams passing through every volume of the assembly;
   c. a detector disposed substantially parallel to the direction of the beam of energetic photons for providing measurements of the intensity of scattered photons of substantially all energies scattered approximately perpendicular to the direction of the beam at each incremental position of the beam; and
   d. a computer for determining the densities in the volume elements of the material in the assembly from a totality of measurements of the intensity of scattered photons scattered approximately perpendicular to the direction of the beam at each incremental position of the beam by a mathematical reconstruction technique.

12. A device according to claim 11, further comprising a transmission detector for detecting energetic photons transmitted through the assembly of objects.

13. A device according to claim 11, wherein the beam of energetic photons comprises energetic photons in the range where the interaction of the energetic photons with the material in the assembly is dominated by the probability for Compton scattering.

14. A device according to claim 11, wherein the detector is segmented in a direction having a component substantially parallel to the beam of energetic photons.

15. A device according to claim 11, wherein the detector is collimated with respect to directions substantially perpendicular to the beam of energetic photons.

16. A device according to claim 11, wherein the mathematical reconstruction technique includes relaxation methods.

17. A device according to claim 11, wherein the mathematical reconstruction technique includes methods of computerized tomographic reconstruction.

* * * * *